US012648822B2

(12) United States Patent
Jin et al.

(10) Patent No.: US 12,648,822 B2
(45) Date of Patent: Jun. 9, 2026

(54) FORCE TACTILE FEEDBACK DEVICE AT MASTER END OF ROBOT ASSISTED SYSTEM FOR VASCULAR INTERVENTIONAL SURGERY

(71) Applicant: SOUTHEAST UNIVERSITY, Jiangsu (CN)

(72) Inventors: Xiaoliang Jin, Jiangsu (CN); Aiguo Song, Jiangsu (CN); Lifeng Zhu, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 331 days.

(21) Appl. No.: 18/544,390

(22) Filed: Dec. 18, 2023

(65) Prior Publication Data

US 2024/0216086 A1 Jul. 4, 2024

Related U.S. Application Data

(63) Continuation of application No. PCT/CN2023/107669, filed on Jul. 17, 2023.

(30) Foreign Application Priority Data

Jan. 3, 2023 (CN) .......................... 202310001183.8

(51) Int. Cl.
*A61B 34/30* (2016.01)
*A61B 34/00* (2016.01)

(52) U.S. Cl.
CPC .............. *A61B 34/30* (2016.02); *A61B 34/76* (2016.02); *A61B 2034/301* (2016.02); *A61B 2034/303* (2016.02)

(58) Field of Classification Search
CPC ... A61B 34/30; A61B 34/76; A61B 2034/301; A61B 2034/303; A61B 34/37; A61B 34/74; A61B 34/77
See application file for complete search history.

(56) References Cited

U.S. PATENT DOCUMENTS

| 2014/0276938 A1 | 9/2014 | Hsu et al. |
| 2019/0258316 A1 | 8/2019 | Suzuki et al. |
| 2023/0070774 A1* | 3/2023 | Li ...................... A61M 25/0113 |

FOREIGN PATENT DOCUMENTS

| CN | 103753519 | 4/2014 |
| CN | 105534599 | 5/2016 |

(Continued)

OTHER PUBLICATIONS

"International Search Report (Form PCT/ISA/210) of PCT/CN2023/107669", mailed on Oct. 31, 2023, pp. 1-5.

(Continued)

*Primary Examiner* — David Hamaoui
*Assistant Examiner* — Olivia Walker
(74) *Attorney, Agent, or Firm* — JCIPRNET

(57) ABSTRACT

A force tactile feedback device at master end of robot assisted system for vascular interventional surgery includes a surgeon operating rod, a circumferential directional surgeon operation action capturing and force tactile feedback unit, a compressible and extendable rhombus structure, a transmission directional surgeon operation action capturing and force tactile feedback unit, a housing and a support plate. The force tactile feedback device at master end of robot assisted system for vascular interventional surgery keeps consistent with a traditional manual vascular interventional surgery in operation mode, and not only reduces a learning cycle and use difficulty for a surgeon on a master end apparatus, but also allows the surgeon to make full use of accumulated experience and skills.

6 Claims, 1 Drawing Sheet

(56)     References Cited

FOREIGN PATENT DOCUMENTS

| CN | 103753519 | B | * | 7/2016 | |
|----|-----------|---|---|--------|---|
| CN | 105534599 | B | * | 1/2018 | ....... A61B 17/00234 |
| CN | 108888347 | | | 11/2018 | |
| CN | 107184274 | B | * | 3/2020 | ............ A61B 34/30 |
| CN | 112587241 | | | 4/2021 | |
| CN | 113133833 | | | 7/2021 | |
| CN | 113729961 | | | 12/2021 | |
| CN | 113729965 | | | 12/2021 | |
| CN | 113729965 | A | * | 12/2021 | ............ A61B 34/37 |
| CN | 115429445 | A | * | 12/2022 | ............ A61B 50/20 |
| CN | 115517770 | | | 12/2022 | |
| CN | 116172721 | | | 5/2023 | |

OTHER PUBLICATIONS

"Written Opinion of the International Searching Authority (Form PCT/ISA/237) of PCT/CN2023/107669", mailed on Oct. 31, 2023, pp. 1-5.

* cited by examiner

FORCE TACTILE FEEDBACK DEVICE AT MASTER END OF ROBOT ASSISTED SYSTEM FOR VASCULAR INTERVENTIONAL SURGERY

CROSS-REFERENCE TO RELATED APPLICATION

This application is a continuation of international application of PCT application serial no. PCT/CN2023/107669 filed on Jul. 17, 2023, which claims the priority benefit of China application no. 202310001183.8 filed on Jan. 3, 2023. The entirety of each of the above mentioned patent applications is hereby incorporated by reference herein and made a part of this specification.

TECHNICAL FIELD

The present disclosure belongs to the technical field of medical apparatuses, and particularly relates to a force tactile feedback device at a master end of a robot assisted system for a vascular interventional surgery.

BACKGROUND

Nowadays, the vascular disease has become a typical disease that jeopardizes human health. The vascular disease is treated through a traditional manually operated vascular interventional surgery and an emerging robot assisted vascular interventional surgery. The emerging robot assisted vascular interventional surgery is a method of utilizing a robot assist system for a vascular interventional surgery to assist the surgeon in completing the surgery in a highly efficient manner, which has obvious advantages over traditional surgical methods, such as preventing the surgeon from being subjected to X-ray radiation, decreasing the burden on the surgeon, and improving the safety of the surgery.

The robot assisted vascular interventional surgery is a remotely operated surgical technique. It involves a process whereby a surgeon operates a master-end apparatus in an X-ray radiation-free environment and remotely controls a slave-end apparatus in an operating room to deliver a guide wire and a catheter to a lesion location of a patient for diagnosis and treatment. Since the robot assisted system for a vascular interventional surgery adopts a master-slave control structure, the excellence of the surgical experience of a surgeon becomes an important factor that directly affects the success rate and even the safety of the surgery. Therefore, the development of a master-end apparatus that improves the surgical experience of a surgeon will greatly improve the success rate and safety of the surgery.

In order to improve the surgical experience of a surgeon during a robot assisted vascular interventional surgery, major research teams at home and abroad have initiated studies on the development of master-end apparatuses. However, most studies have only achieved motion control of a master-end apparatus over a slave-end apparatus, relying only on image guidance for delivery of a guide wire and a catheter to a lesion location of a patient, but lacking a tactile feedback function. Moreover, from the point of view of satisfying operating habits of surgeons, most of the studies ignore the design idea of ergonomics of a master-end apparatus, and use a commercialized tactile feedback device as the master-end apparatus, which increases the learning cycle and the difficulty of using the master-end apparatus by a surgeon.

SUMMARY

In order to solve the above problems, disclosed in the present disclosure is a force tactile feedback device at a master end of a robot assisted system for a vascular interventional surgery, which not only satisfies the design idea ergonomics at a master-end apparatus, but also has a tactile feedback function. Surgical experience of a surgeon can be improved, a success rate and safety of a surgery can be guaranteed, and a learning cycle and difficulty of using a master-end device by a surgeon can also be reduced.

For achieving the above objective, the present disclosure provides a technical solution as follows.

A force tactile feedback device at a master end of a robot assisted system for a vascular interventional surgery includes a surgeon operating rod, a surgeon operation action capturing and force tactile feedback unit in a circumferential direction, a rhombus structure capable of being compressed and extended, and a surgeon operation action capturing and force tactile feedback unit in a transmission direction.

The surgeon operating rod has a cylindrical structure similar to a guide wire and a catheter, is a part directly operated by a surgeon, and has two degrees of freedom of motion, that is, motion in a circumferential direction and motion in a transmission direction.

The surgeon operation action capturing and force tactile feedback unit in a circumferential direction includes a brushed direct current motor I, a solid shaft incremental photoelectric encoder I, a housing I, a synchronous pulley I, a synchronous pulley II and a support plate IV, where the housing I covers the outside, the solid shaft incremental photoelectric encoder I and the brushed direct current motor I are fixed to the support plate IV, an output shaft of the solid shaft incremental photoelectric encoder I is connected to both the synchronous pulley I and the surgeon operating rod, and an output shaft of the brushed direct current motor I is connected to the synchronous pulley II. Under the action of a synchronous belt, synchronous rotation with the solid shaft incremental photoelectric encoder I is implemented. During a surgery, when a surgeon holds the operating rod to rotate clockwise or counterclockwise in a circumferential direction, the solid shaft incremental photoelectric encoder records a rotation angle of the operating rod. When the guide wire and the catheter at a slave end are subjected to force in the circumferential direction, an output torque of the brushed direct current motor changes accordingly, to provide real-time force tactile feedback for the surgeon by means of the synchronous belt.

Two ends of the rhombus structure capable of being compressed and extended are respectively connected to the surgeon operation action capturing and force tactile feedback unit in a circumferential direction and the surgeon operation action capturing and force tactile feedback unit in a transmission direction by means of a support plate I and a support plate II.

The surgeon operation action capturing and force tactile feedback unit in a transmission direction includes a brushed direct current motor II, a solid shaft incremental photoelectric encoder II, a linear guide rail module, a housing II, a support plate I and a support plate III, where the housing II covers the outside, the solid shaft incremental photoelectric encoder II and the brushed direct current motor II are fixed to the support plate I, output shafts of the solid shaft incremental photoelectric encoder II and the brushed direct current motor II are respectively connected to one ends of the rhombus structure capable of being compressed and extended, and the linear guide rail module is fixed to the support plate III at the bottom. During a surgery, when a surgeon holds the operating rod to do push-pull motion in a transmission direction, the rhombus structure is compressed or extended, and the solid shaft incremental photoelectric encoder II connected to the rhombus structure records displacement of the operating rod. When the guide wire and the catheter at the slave end are subjected to force in the transmission direction, an output torque of the brushed direct current motor II changes accordingly, to provide real-time force tactile feedback for the surgeon by means of the rhombus structure.

The housing is an internal main component used for encapsulating the surgeon operation action capturing and force tactile feedback unit in a circumferential direction and the surgeon operation action capturing and force tactile feedback unit in a transmission direction, such that the design of the master-end force tactile feedback device is relatively attractive.

The support plate is configured to fix and connect major components such as the solid shaft incremental photoelectric encoders, the brushed direct current motors, the linear guide rail module, bearings, and the rhombus structure capable of being compressed and extended.

The beneficial effects of the present disclosure:

1. In a traditional manual vascular interventional surgery, main surgical actions of a surgeon include: pushing, pulling, clockwise rotation, and counterclockwise rotation of a guide wire and a catheter. An operating rod similar to a guide wire and a catheter is used as a part directly operated by a surgeon and has two degrees of freedom of motion. The operation mode of the operating rod is consistent with that of a traditional vascular interventional surgery, such that a learning period and difficulty of using the master-end apparatus by a surgeon can be reduced, and the surgeon can fully use accumulated experience and skills. The novel force tactile feedback device at a master end of a robot assisted system for a vascular interventional surgery satisfies the design idea of ergonomics in structure.

2. The novel force tactile feedback device at a master end of a robot assisted system for a vascular interventional surgery in the present disclosure takes into account an influence of force tactile feedback on safety of a surgery, uses torque characteristics of the brushed direct current motors to reproduce real-time force conditions of the guide wire and the catheter at the slave end to the master end, and acts on a hand of a surgeon, so as to improve the surgical experience of a surgeon and guarantee the safety of a surgery.

DETAILED DESCRIPTION OF THE EMBODIMENTS

Figures 1, 2:
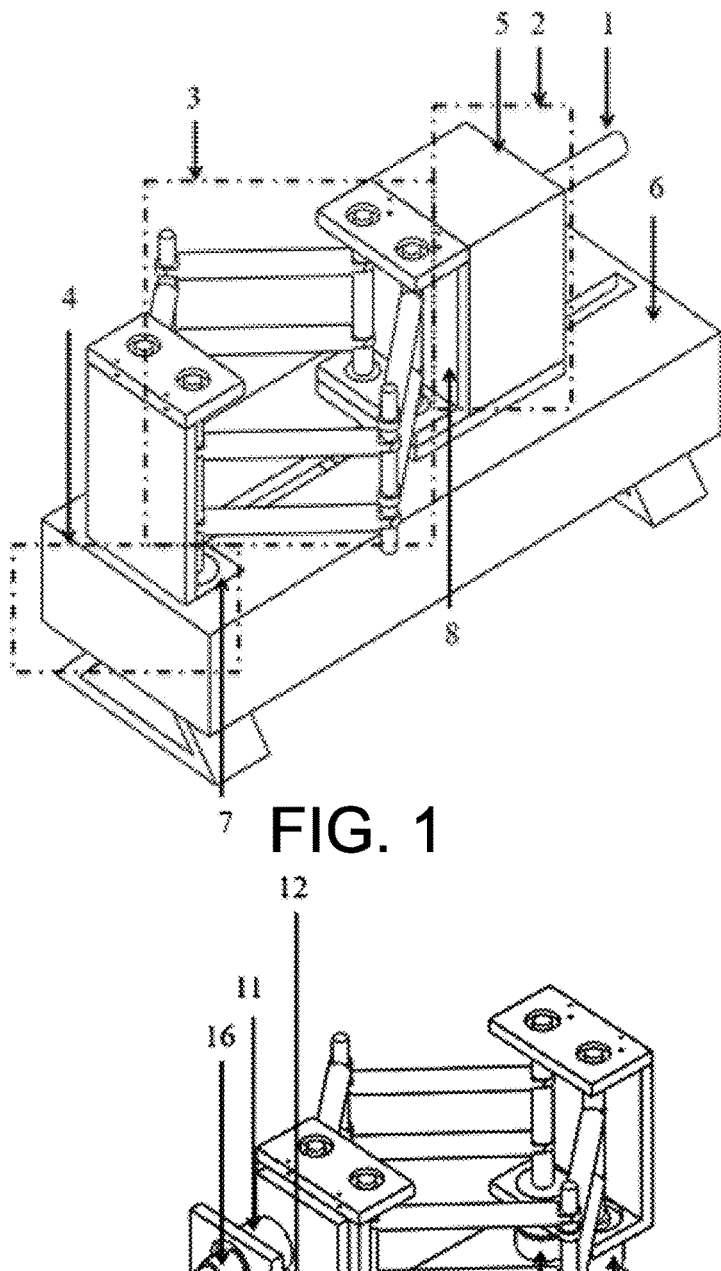
FIG. 1 is three-dimensional structural diagram 1 of the present disclosure.
FIG. 2 is three-dimensional structural diagram 2 of the present disclosure.

The present disclosure is further elucidated below in conjunction with drawings and specific embodiments. It should be understood that these specific embodiments below are provided merely to illustrate the present disclosure rather than to limit the scope of the present disclosure.

As shown in FIGS. 1 and 2, as for the force tactile feedback device at a master end of a robot assisted system for a vascular interventional surgery according to the present disclosure, in the surgeon operation action capturing and force tactile feedback unit 2 in a circumferential direction, the solid shaft incremental photoelectric encoder I 11 and the brushed direct current motor I 12 are fixed to the support plate IV 10, an output shaft of the solid shaft incremental photoelectric encoder I 11 is connected to both the synchronous pulley I 16 and the surgeon operating rod 1, an output shaft of the brushed direct current motor I 12 is connected to the synchronous pulley II 17, the output shafts of the solid shaft incremental photoelectric encoder I 11 and the brushed direct current motor I 12 rotate synchronously under the action of the synchronous belts, and the housing I 5 encapsulates the surgeon operation action capturing and force tactile feedback unit 2 in a circumferential direction. An end and an opposite end of the rhombus structure 3 capable of being compressed and extended are respectively connected to the surgeon operation action capturing and force tactile feedback unit 2 in a circumferential direction and the surgeon operation action capturing and force tactile feedback unit 4 in a transmission direction by means of the support plate I 7 and the support plate II 8. In the surgeon operation action capturing and force tactile feedback unit 4 in a transmission direction, the solid shaft incremental photoelectric encoder II 13 and the brushed direct current motor II 14 are fixed to the support plate I 7, output shafts of the solid shaft incremental photoelectric encoder II 13 and the brushed direct current motor II 14 are connected to the diamond structure 3 capable of being compressed and extended separately, the linear guide rail module 15 is fixed is configured to implement push-pull motion of the surgeon operating rod 1 in the transmission direction, and the housing II 6 encapsulates the surgeon operation action capturing and force tactile feedback unit 4 in a transmission direction.

Surgical actions of a surgeon are captured as follows: when the surgeon holds the operating rod 1 to rotate clockwise or counterclockwise along an axis in a circumferential direction, in the surgeon operation action capturing and force tactile feedback unit 2 in a circumferential direction, the solid shaft incremental photoelectric encoder I 11 records a rotation angle of the surgeon operating rod 1. When the surgeon holds the operating rod 1 to do push-pull motion in a transmission direction, the surgeon operation action capturing and force tactile feedback unit 2 in a circumferential direction arranged on the linear guide rail module 15 is pushed simultaneously, the rhombus structure 3 is compressed or extended, and in the surgeon operation action capturing and force tactile feedback unit 4 in a transmission direction connected to the rhombus structure 3, the solid shaft incremental photoelectric encoder II 13 records displacement of the operating rod.

Force tactile feedback to a surgeon is achieved as follows: when a guide wire and a catheter at a slave end are subject to force in a circumferential direction, in the surgeon operation action capturing and force tactile feedback unit 2 in a circumferential direction, an output torque of the brushed direct current motor I 12 changes and acts on the surgeon-held operating rod 1 by means of a synchronous belt, so as to provide real-time force tactile feedback in the circumferential direction for a surgeon. When the guide wire and the catheter at the slave end are subject to force in a transmission direction, in the surgeon operation action capturing and force tactile feedback unit 4 in a transmission direction connected to the rhombus structure 3, an output torque of the brushed direct current motor II 14 changes and acts on the surgeon-held operating rod 1 by means of the rhombus structure 3 capable of being compressed and extended, so as to provide real-time force tactile feedback in the transmission direction for the surgeon.

Specifically, a diameter and a length of the surgeon operating rod 1 are 1.5 cm and 10 cm respectively.

Specifically, a diameter and a length of each arm of the rhombus structure 3 capable of being compressed and extend are 1.5 cm and 14.5 cm respectively.

Specifically, a length of the linear guide rail module 15 is 30 cm.

Specifically, the solid shaft incremental photoelectric encoders 11 and 13 have the pulse number of 2500, an output mode of NPN type, output shafts with a diameter of 6 mm, and a working voltage of 5V.

Specifically, the brushed direct current motors 12 and 14 have a stall torque of 1090 mN·m, a gear box with a reduction ratio of 5.8:1, an output shaft with a diameter of 6 mm, and a rated voltage of 42 V.

Specifically, a length, a width and a height of a housing of the surgeon operation action capturing and force tactile feedback unit 2 in a circumferential direction are 14.5 cm, 10 cm and 11 cm respectively.

Specifically, a length, a width and a height of a housing of the surgeon operation action capturing and force tactile feedback unit 4 in a transmission direction are 50 cm, 20 cm and 14.5 cm respectively.

It should be noted that the above contents merely illustrate the technical idea of the present disclosure and cannot limit the scope of protection of the present disclosure. A person of ordinary skill in the art may further make several improvements and modifications without departing from the principle of the present disclosure, and such improvements and modifications should fall within the scope of protection of the claims of the present disclosure.

The invention claimed is:

1. A force tactile feedback device at master end of robot assisted system for vascular interventional surgery, comprising:
   a surgeon operating rod, comprising a cylindrical structure and having one degree of freedom of motion in a circumferential direction and one degree of freedom of motion in a transmission direction;
   a circumferential directional surgeon operation action capturing and force tactile feedback unit, comprising a first brushed direct current motor, a first solid shaft incremental photoelectric encoder, a first housing, a first synchronous pulley, a second synchronous pulley and a fourth support plate, wherein the first housing covers the first brushed direct current motor, the first solid shaft incremental photoelectric encoder, the first synchronous pulley, the second synchronous pulley and the fourth support plate, the first solid shaft incremental photoelectric encoder and the first brushed direct current motor are fixed to the fourth support plate, an output shaft of the first solid shaft incremental photoelectric encoder is connected to both the first synchronous pulley and the surgeon operating rod, and an output shaft of the first brushed direct current motor is connected to the second synchronous pulley;
   a compressible and extendable rhombus structure, wherein two ends of the compressible and extendable rhombus structure are respectively connected to the circumferential directional surgeon operation action capturing and force tactile feedback unit and a transmission directional surgeon operation action capturing and force tactile feedback unit by means of a first support plate and a second support plate; and the transmission directional surgeon operation action capturing and force tactile feedback unit, comprising a second brushed direct current motor, a second solid shaft incremental photoelectric encoder, a linear guide rail module, a second housing, the first support plate and a third support plate, wherein the second housing covers the second brushed direct current motor, the second solid shaft incremental photoelectric encoder, the linear guide rail module, the first support plate and the third support plate, the second solid shaft incremental photoelectric encoder and the second brushed direct current motor are fixed to the first support plate, output shafts of the second solid shaft incremental photoelectric encoder and the second brushed direct current motor are respectively connected to one of the ends of the compressible and extendable rhombus structure, and the linear guide rail module is fixed to the third support plate at a bottom.

2. The force tactile feedback device at master end of robot assisted system for vascular interventional surgery according to claim 1, wherein in the circumferential directional surgeon operation action capturing and force tactile feedback unit, the output shafts of the first solid shaft incremental photoelectric encoder and the first brushed direct current motor rotate synchronously under an action of a synchronous belt, and the first housing encapsulates the circumferential directional surgeon operation action capturing and force tactile feedback unit; and in the transmission directional surgeon operation action capturing and force tactile feedback unit, the linear guide rail module is configured to implement push-pull motion of the surgeon operating rod in the transmission direction, and the second housing encapsulates the transmission directional surgeon operation action capturing and force tactile feedback unit.

3. The force tactile feedback device at master end of robot assisted system in vascular interventional surgery according to claim 1, wherein when the surgeon operating rod is rotated clockwise or counterclockwise along an axis in the circumferential direction, in the circumferential directional surgeon operation action capturing and force tactile feedback unit, the first solid shaft incremental photoelectric encoder records a rotation angle of the surgeon operating rod; and when the surgeon operating rod is operated in a push-pull motion along a straight line in the transmission direction, the circumferential directional surgeon operation action capturing and force tactile feedback unit arranged on the linear guide rail module is pushed simultaneously, the compressible and extendable rhombus structure is compressed or extended, and in the transmission directional surgeon operation action capturing and force tactile feedback unit connected to the compressible and extendable rhombus structure, the second solid shaft incremental photoelectric encoder records displacement of the surgeon operating rod.

4. The force tactile feedback device at master end of robot assisted system in vascular interventional surgery according to claim 1, wherein when a guide wire and a catheter at a slave end are subject to force in the circumferential direction, in the circumferential directional surgeon operation action capturing and force tactile feedback unit, an output torque of the first brushed direct current motor changes accordingly and acts on the surgeon operating rod by means of a synchronous belt, so as to provide real-time force tactile feedback in the circumferential direction; and when the guide wire and the catheter at the slave end are subject to force in the transmission direction, in the transmission directional surgeon operation action capturing and force tactile feedback unit connected to the compressible and extendable rhombus structure, an output torque of the second brushed direct current motor changes accordingly and acts on the surgeon operating rod by means of the compressible and extendable rhombus structure, so as to provide real-time force tactile feedback in the transmission direction.

5. The force tactile feedback device at master end of robot assisted system for vascular interventional surgery according to claim 1, wherein each of the first and the second solid shaft incremental photoelectric encoders has a pulse number of 2500, the output shaft with a diameter of 6 mm, and a working voltage of 5 V.

6. The force tactile feedback device at master end of robot assisted system for vascular interventional surgery according to claim 1, wherein each of the first and the second brushed direct current motors has a stall torque of 1090 mN·m, a gear box with a reduction ratio of 5.8:1, the output shaft with a diameter of 6 mm, and a rated voltage of 42 V.

\* \* \* \* \*